United States Patent [19]

Hager et al.

[11] Patent Number: 5,358,860
[45] Date of Patent: Oct. 25, 1994

[54] STEREOSELECTIVE EPOXIDATION OF ALKENES BY CHLOROPEROXIDASE

[75] Inventors: Lowell P. Hager, Urbana; Eric J. Allain, Champaign, both of Ill.

[73] Assignee: The Board of Trustees of the University of Illinois, Urbana-Champaign, Ill.

[21] Appl. No.: 43,049

[22] Filed: Apr. 5, 1993

[51] Int. Cl.$^5$ .................... C12N 9/08; C12P 17/02
[52] U.S. Cl. ............................ 435/123; 435/192; 435/280
[58] Field of Search .............. 435/123, 132, 192, 280

[56] References Cited

U.S. PATENT DOCUMENTS

| | | | |
|---|---|---|---|
| 3,623,949 | 11/1971 | Kollonitsch | 435/131 |
| 4,247,641 | 1/1981 | Neidleman et al. | 435/123 |
| 4,284,723 | 8/1981 | Neidleman et al. | 435/123 |
| 4,426,449 | 1/1984 | Geigert et al. | 435/155 |
| 4,587,217 | 5/1986 | Geigert et al. | 435/155 |
| 4,707,447 | 11/1987 | Hunter et al. | 435/132 |
| 4,937,191 | 6/1990 | Geigert et al. | 435/132 |
| 5,110,740 | 5/1992 | Pokoda et al. | 435/262 |

OTHER PUBLICATIONS

Geigert et al "Biochem & Biophys Res. Comm." vol. 136 No. 2 Apr. 29, 1986 pp. 778-782.
Ortiz de Montellano et al "Jour Biol Chem" vol. 267 No. 24 Aug. 25, 1987 pp. 11641-11646.
Colonna et al "Tetrahed. Asym" vol. 4 No. 6 pp. 1325-1330 Jun. 1993.
Allain et al "J. Am Chem. Soc." 1993 vol. 115 pp. 4415–4416.
Kolonitsch et al. "J. Am. Chem Soc." vol. 92 Jul. 15, 1970, No. 14 pp. 4489-4490.
Bolm, C. "Katalytische Enantioselektive Eposidierungen einfacher Olefine," *Agnew. Chem. Int. Ed. Engl.* 1991, 30, 403.
Henbest et al., "A Solvent Trend in the Epoxidation of Substituted Alkenes," *J. Chem. Soc., Chem. Commun.*, 1967, 1085-1086.
Katsuki et al., "The First Practical Method for Asymmetric Epoxidation," *J. Am. Chem. Soc.* 102, 1980, 5974-5976.
Gao et al., "Catalytic Asymmetric Epoxidation and Kinetic Resolution: Modified Procedures Including In Situ Derivatization," *J. Am. Chem. Soc.* 109, 1987, 5765-5780.
Groves and Myers, "Catalytic Asymmetric Expoxidations with Chiral iron Porphyrins," *J. Am. Chem. Soc.* 105, 1983, 5781-5796.
Groves and Visk, "Asymmetric Hyrdoxylation, Epoxidation, and Sulfoxidation Catalyzed by Vaulted Binaphthyl Metalloporphyrins," *J. Org. Chem* 55, 1990, 3628-3634.
Tani et al., "Asymmetric Epoxidation of Hydrocarbon Olefins by Tert-Butyl Hydroperoxide with Molybdenum (VI) Catalysts in the Presence of Optically Active Diols. Application to the Asymmetric Synthesis of (35)-2,3-Oxidosqualene," *Tetrahedron Lett.* 32, 1970, 3017-3020.
Meunier, B., et al., "Sodium Hypochloriate: A Convenient Oxygen Source for Olefin Epoxidation Catalyzed by (Porphyrinato)manganese Complexes," *J. Am. Chem. Soc.*, 106, 1984, 6668-6676.

(List continued on next page.)

Primary Examiner—Herbert J. Lilling
Attorney, Agent, or Firm—Keck, Mahin & Cate

[57] ABSTRACT

A method of converting olefins to chiral epoxides comprises combining an asymmetric aliphatic or aryl alkene substrate with a buffered chloroperoxidase solution to form a stabilized reaction mixture, and gradually adding hydrogen peroxide as a substrate oxidant, such that the chloroperoxidase catalyzes the conversion of the substrate to the corresponding epoxide in enantiomeric excess. The products of the invention are alkyl and aryl non-primary epoxides. The resulting preparations are enantiomerically pure, and may greatly enhance large-scale synthesis of stereoisomer products such as pharmaceuticals and pesticides.

22 Claims, No Drawings

OTHER PUBLICATIONS

Curci et al., "Asymmetric Epoxidation of Unfunctionalized Alkenes by Dioxirane Intermediates . . . Ketones," *J. Chem. Soc. Chem. Commun.*, 1984, 155–156.

Sinigalia et al., "Asymmetric Epoxidation of Simple Olefins Catalyzed by Chiral Diphosphone-Modified Platinum(II) Complexes," *Organometallics*, 6, 1987, 728–734.

O'Malley and Kodadek, "Synthesis and Characterization of the 'Chiral Wall' Porphyrin: A Chemically Robust Ligand for Metal-Catalyzed Asymmetric Epoxiations," *J. Am. Chem. Soc.* 111, 1989, 9116–9117.

Naruta et al., "Remarkable Effects of Metal Ions and Axial Bases on Catalytic and Asymmetric Oxidation of Simple Olefins with a 'Twin-coronet' Porphyrin," *J. Am. Chem. Soc.* 113, 1991, 6865–6879.

Zhang et al., "Enantioselective Epoxidation of Unfunctionalized Olefins Catalyzed by (Salen)manganese Complexes," *J. Am. Chem. Soc.* 112, 1990, 2801–2803.

Zhang et al., "Asymmetric Olefin Epoxidation with Sodium Hypochlorite Catalyzed by Easily Prepared Chiral Mn(III) Salen Complexes," *J. Org. Chem.* 56, 1991, 2296–2298.

Jacobsen et al., "Highly Enantioselective Epoxidation Catalysts Derived from 1,2-Diaminocyclohexane," *J. Am. Chem. Soc.* 113, 1991, 7063–7064.

Irie et al., "Catalytic Asymmetric Epoxidation of Unfunctionalized Olefins," *Tetrahedron Lett.* 31, 1990, 7345–7348.

Irie et al., "Enantioselective Epoxidation of Unfunctionalized Olefins Using Chiral (Salen)Mananese(III) Complexes," *Tetrahedron Lett. 32, 1991, 1055–1058.*

Irie et al., "Donor Ligand Effect in Asymmetric Epoxidation of Unfunctionalized Olefins with Chiral Salen Complexes," *Synlett* 2, 1991, 265–266.

Konishi et al., "Asymmetric Epoxidation of Olefins Catalyzed by Manganese Complexes of Chiral 'Strapped' Porphyrins with Diastereotopic Faces. A Novel Strategy for Stereochemical Modeling of the Active Sites of Cytochrome P–450," *J. Am. Chem. Soc.* 114, 1992, 1313–1317.

Halterman et al., "Catalytic Asymmetric Epoxidations of Unfunctionalized Alkenes Using the First $D_4$-Symmetric Metallotetraphenylporphyrin," *J. Org. Chem.* 56, 1991, 5253–5254.

Colletti, S. L. and Halterman, T. L., "Asymmetric Epoxidation of Unfunctionalized Alkenes Using the New $C_2$-Symmetrical 1,1'-Binaphthyl-2,3'-Dimethylene-Bridged anas-Bis(1-indenyl)Titanium Dichloride Catalyst," *Tetrahedron Lett.* 33, 1992, 1005.

Ortiz de Montellano et al., "Theoretical and experimental Analysis of the Absolute Stereochemistry of cis-$\beta$-Methylstyrene Epoxidation by Cytochrome P450cam," *J. Am. Chem. Soc.* 113, 1991, 3195.

Boyd et al., "Chemical Synthesis and Optical Purity Determination of Optically Active 1,2-Epoxyindan and Alcohol Products which are also Derived from Mammalian or Microbial Metabolism of Indene of Indanones," *J. Chem. Soc. Perkin Trans.* 1, 1982, 2767.

Schurig, V., Wistuba, D., "Asymmetrical mikrosomale Epoxidierung einfacher prochiraler Olefine," *Angew. Chem. Int. Ed. Engl.*, 23, 1984, 796.

Takahasi et al., "Stereocontrol of a Tertiary Hydroxyl Group Via Epoxidation," *Tetrahedron Lett.* 30, 1989, 1583.

Ohta, H., Tetsukawa, H. J., "Microbial Epoxidation of Long-chain Terminal Olefins," *Chem. Soc. Chem. Commun.*, 1978, 849.

Wislocki and Lu, "Epoxidation Reactions Catalyzed by Rat Liver Cytochromes P-450 and P-448 Occur at different Faces of the 8,9-double bond of 8-methylbenz[a]anthracene," *Proc. Natl. Acad. Sci. USA* 79, 1982, 6802–6806.

Gelb et al., "Cytochrome P450$_{cam}$ Catalyzed Epoxidation of Dehydrocamphor," *Biochem. Biophys. Res. Commun.*, 1982.

Ortiz de Montellano et al., "Stereochemistry of Cytochrome P–450-catalyzed Epoxidation and Prosthetic Heme Alkylation," *J. Biol. Chem.* 258, 1983, 4208–4213.

Yang and Chiu, "Cytochrome P–450-Catalyzed Stereoselective Epoxidation at the K Region of Benz[a]anthracene and Benzo[a]pyrene," *Arch. Biochem. Biophys.* 240, 1985, 546–552.

Yang, "Stereoselectivity of Cytochrome P-450 Isozymes and Epoxide Hydrolase in the Metabolism of Polycyclic Aromatic Hydrocarbons," *Biochem. Pharmacol.* 37, 1988, 61–70.

Wistuba et al., "Cytochrome P–450-Catalyzed Asymmetric Epoxidation of Simple Prochiral and Chiral Aliphatic Alkenes: Species Dependence and Effect of Enzyme Induction on Enantioselective Oxirane Formation," *Chirality* 1, 1989, 127–136.

(List continued on next page.)

OTHER PUBLICATIONS

Capdevila et al., "Cytochrome P-450 Enzyme-specific Control of the Regio- and Enantiofacial Selectivity of the Microsomal Arachidonic Acid Epoxygenase," *J. Biol. Chem.* 265, 1990, 10865–10871.

Ortiz de Montellano and Grab, "Cooxidation of Styrene by Horseradish Peroxidase and Phenols: A Biochemical Model for Protein-Mediated Cooxidation," *Biochemistry* 26, 1987, 5310–5314.

Panthananickal et al., "Stereoselectivity of the Epoxidation of 7,8-Dihydrobenzo[a]pyrene by Prostaglandin H Synthase and Cytochrome P-450 Determined by the Identification of Polyguanylic Acid Adducts," *J. Biol. Chem.* 258, 1983, 4411–4418.

Mallet et al., "Activation of ($\pm$)-trans-7,8-dihydroxy-7,8-dihydrobenzo[a]pyrene to diolepoxides by human polymorphonuclear leukocytes or myeloperoxidase," *Carcinogenesis* 12, 1991, 521–524.

Ohta and Tetsukawa, "Microbial Epoxidation of Long-chain Terminal Olefins," *J.C.S. Chem. Comm.*, 1978, 849–850.

Stirling and Dalton, "The Fortuitous Oxidation and Cometabolism of Various Carbon Compounds by Whole-Cell Suspensions of *Methylococcus capsulatus* (Bath)," *FEMS Microbiology Letters*, 1979, 5:315–318.

Hou et al., "Microbial Oxidation of Gaseous Hydrocarbons: Epoxidation of $C_2$ to $C_4$ n-Alkenes by Methylotrophic Bacteria", *App. and Envir. Microbiol.*, 1979, 38:127–134.

De Smet et al., "Synthesis of 1,2-Epoxyoctane by *Pseudomonas oleovorans* During Growth in a Two-Phase System Containing High Concentrations of 1-Octene," *App. and Envir. Microbiol.*, 1981, 42:811–816.

Furuhashi et al., "Production of 1,2-Epoxyalkanes from 1-Alkenes by *Norcardia corallina* B-276," *E. J. Appl. Microbiol. Biotechnol.*, 1981, 12:39–45.

Fu et al., "*Pseudomonas oleovorans* Monooxygenase Catalyzed Asymmetric Epoxidation of Allyl Alcohol Derivatives and Hydroxylation of a Hypersensitive Radical Probe with the Radical Ring Opening Rate Exceeding the Oxygen Rebound Rate," *J. Am. Chem. Soc.*, 1991, 113:5878–80.

Morris, D. R., Hager, L. P., "Mechanism of the Inhibition of Enzymatic halogenation by Antithyroid Agents," *J. Biol. Chem.*, 1966, 241, 3582.

Blanke, S. R., Yi, S., Hager, L. P., "Development of Semi-Continuous and Continuous Flor Bioreactions for the High Level Production of Chloroperoxidase," *Biotechnology Lett.*, 1989, 11:769.

Thomas, J. A., et al., "Chloroperoxidase," *J. Biol. Chem.*, 1970, 245:3129.

Kedderis, G. L., and Hallenberg, P. F., "pH Kinetic Studies of the N-Demetehylation of N,N-Dimethylaniline Catalyzed by Chloroperoxidase," *Arch. Bioch. Biophys.*, 1984, 233, 315.

McCarthy and White, "Functional Difference between Peroxidase Compound I and the Cytochrome P-450 Reactive Oxygen Intermediate," *J. Biol. Chem.*, 1987, 258, 9153–9158.

Elfarra et al., "Mechanisms of 1,3-Butadiene Oxidations to Butadiene Monoxide and Crotonaldehyde by Mouse Liver Microsomes and Chloroperoxidase," *Arch. Bioch. Biophys.*, 1991, 286, 244–251.

Collonna et al., "Chloroperoxidase and Hydrogen Peroxide: An Efficient System for Enzymatic Enantioselective Sulfoxidations," *Tetrahedron: Asymmetry*, 1992, 3, 95.

Hager et al., "Chloroperoxidase," *J. Biol. Chem.*, 1966, 241, 1769.

Neidleman, S. L. and Geigert, J., *Biohalogenation: Principles, Basic Roles and Applications*, John Wiley and Sons, p. 109.

Ramakrishnan et al., "Stereoselectivity of Chloroperoxidase-Dependent Halogenation," *Biochemistry*, 1983, 22, 3271–3277.

STEREOSELECTIVE EPOXIDATION OF ALKENES BY CHLOROPEROXIDASE

FIELD OF THE INVENTION

This invention provides a biological process of stereospecific olefin epoxidation, useful for large-scale synthesis. The invention relates to the use of an enzyme, chloroperoxidase, with appropriate substrates and reaction conditions that stabilize the enzyme, to catalyze the highly enantioselective epoxidation of alkenes.

BACKGROUND OF THE INVENTION

Many organic compounds exist in the form of enantiomers, pairs of stereoisomers that are mirror-images of each other. Such compounds are said to exhibit the property of being chiral, which can be measured by optical rotation of plane polarized light. Chirality is of vital importance in the manufacture of pharmaceuticals, pesticides, and other biochemicals. Indeed, with many compounds, a +(or right-handed) enantiomer may have one biological activity, while the —(or left-handed) enantiomer has a completely different activity. Racemic mixtures of enantiomers, comprising half of each type, are relatively easy to prepare by existing methods, but are of little use in preparing pure enantiomeric intermediates and final products. Synthesis of pure enantiomer preparations requires use of chiral substrates, either as starting materials or as intermediates.

One useful step in industrially-relevant synthesis of organic chemicals is the oxidation of alkenes, otherwise known as olefins, to produce the corresponding epoxide. Accordingly, the search for methods of asymmetric synthesis of epoxides from olefins has been the subject of many chemical and biological studies. Olefins are abundantly available as natural products and as compounds produced by the chemical industry. Asymmetric epoxides, whether produced from olefins or by other reactions, have many advantages as electrophilic intermediates for stereochemical chemical syntheses involving reactions with nucleophiles.

1. Chemical Synthesis

Chemical epoxidation reactions using synthetic catalysts have been used to produce chiral epoxides. (Bolm, C. *Angew. Chem. Int. Ed. Engl.* 1991, 30, 403). These reactions require catalysts, produce generally poor yields, and require substituted or large olefins to be effective.

The development of chemical methods for the production of chiral epoxides started with the work of Henbest et al. (1967 *J. Chem. Soc., Chem. Commun.* 1085–1086) who developed homochiral (enantiomerically pure) percamphoric acid as a method for asymmetric epoxide synthesis. The enantiomeric purity of epoxide product was poor.

Sharpless and coworkers (Katsuki et al. 1980. *J. Am. Chem. Soc.* 102, 5974–5976; and Gao et al. 1987 *J. Am. Chem. Soc.* 109, 5765–5780) developed a catalytic chemical oxidation for the synthesis of asymmetric epoxides, using a metal (titanium) and allelic alcohols—those with an -OH group on the carbon adjacent to the alkene double-bond.

Groves and Myers (1983 *J. Am. Chem. Soc.* 105, 5791–5796) modified iron porphyrins to include optically active functionalities at the meso positions and investigated asymmetric epoxidations of prochiral olefins with these catalysts. Various substituted styrenes and aliphatic olefins were epoxidized with ee (enantiomeric excess, the difference between the concentration of one enantiomer and the other) values ranging between 0% for 1-methyl cyclohexene oxide and 51% for p-chlorostyrene oxide. Groves and Visk (1990 *J. Org. Chem.* 55, 3628–3634) used a chiral, vaulted binaphthyl porphyrin derivative to obtain enantiomeric excesses in the range of 20–72% for catalytic asymmetric epoxidations of certain olefins.

Tani et al. (1979 *Tetrahedron Lett.* 32, 3017–3020) reacted prochiral squalene, a 25 carbon linear olefin with multiple alkene double bonds, with ter-butyl peroxide and molybdenum (VI) catalysts in the presence of optically active diols to produce chiral epoxides.

Curci et al. (1984 J. Chem. Sot., Chem. Commun., 155–156.) reported the asymmetric epoxidation of unfunctionalized alkenes by dioxirane intermediates generated from potassium peroxomonosulphate and chiral ketones. Enantiomeric excesses were low, in the range 9–12%.

Sinigalia et al. (1987 *Organometallics*, 6, 728–734) describe the asymmetric epoxidation of simple olefins catalyzed by chiral diphosphine-modified platinum(II) complexes. They carried out the epoxidation of 1-octene and propene with dilute hydrogen peroxide and formed epoxide product with ee% as high as 41%.

O'Malley and Kodadek (1989 *J. Am. Chem. Soc.* 111, 9116–9117) report the synthesis and characterization of a "chiral wall" consisting of a tetra naphthalene derivation of porphyrin which can function as a catalyst in sodium hypochlorite epoxidation reactions. The reaction gives only partial asymmetric synthesis and a turnover number around 13–14 events per min.

Naruta et al. (1991 *J. Am. Chem. Soc.* 113, 6865–6879) modeled cytochrome P-450 epoxidations by preparing a chiral $C_2$ symmetric "twin coronet" porphyrin having chiral biaryl auxiliaries linked by ethereal bonds on both faces. They obtained enantiomeric excesses as high as 72% with some styrene derivatives.

Zhang et al. (1990 *J. Am. Chem. Soc.* 112, 2801–2803) used (salen)manganese complexes for enantioselective epoxidation of unfunctionalized olefins. Their first report described the synthesis of manganese complexes of chiral Schiff bases that catalyze epoxidation of alkyl- and aryl-substituted olefins. In a subsequent publication, Zhang et al. (1991 *J. Org. Chem.* 56, 2296–2298) described a method for the asymmetric epoxidation of cis-beta-methylstyrene with yields as high as 86% using NaOCl (sodium hypochlorite) and a chiral Mn(III) salen complex. They reported approximately 35 turnovers before the catalyst became inactivated. A revised procedure using catalysts derived from 1,2-diaminocyclohexane was reported by Jacobsen et al. (1991 *J. Am. Chem. Soc.* 113, 7063–7064).

Irie et al. (1990. Tetrahedron Lett. 31, 7345–7348) also reported catalytic asymmetric epoxidation of unfunctionalized olefins using manganese-salen complexes. Their highest enantioselectivity of 50% was realized with phenyl propene. Other salen catalysts have been developed by Irie and coworkers (1991 *Tetrahedron Lett.* 32. 1055–1058; 1991 Synlett 2, 265–266).

Konishi et al. (1992 *J. Am. Chem. Soc.* 114, 1313–1317) report on the asymmetric epoxidation of prochiral olefins such as styrene derivatives and vinyl naphthalene by iodosylbenzene. Oxidation was achieved by using the manganese complexes of the antipodes of p-xylylene-strapped porphyrin as catalysts in the presence of imidazole. The optically active epoxides were obtained in 42–58% ee.

Another chiral porphyrin catalyst has been reported by Halterman et al. (1991 *J. Org. Chem.* 56, 5253–5254). They prepared a chiral tetraphenylporphyrin exhibiting $D_4$ symmetry. A manganese chloride complex of this porphyrin catalyzed alkene epoxidations and gave enantioselectivities in the range of 41 to 76%.

Recently developed synthetic catalysts allow for the epoxidation of some conjugated olefins (those with alternating single and double bonds) but olefins bearing only aliphatic substituents are poor substrates for these catalysts and other synthetic catalysts as well. (Colletti, S. L. and Halterman, R. L. Tetrahedron Lett. 1992, 33, 1005; Sinigalia et al. *Organometallics* 1987, 6, 728).

In sum, chemical synthetic methods are not highly enantioselective. The turnover rates are low, typically in the range of 1 to 20 turnovers per minute. The chemical catalysts are rapidly inactivated in the reactions, and high catalyst to substrate ratios are necessary.

2. Enzyme catalysis

Biological catalysis has been employed for epoxidation, employing purified enzymes or whole cells. (Ortiz de Montellano et al. *J. Am. Chem Soc.* 1991, 113, 3195; Boyd et al. *J. Chem. Soc. Perkin Tram.* 1, 1982, 2767; Schurig, V., Wismba, D. *Angew. Chem. Int. Ed. Engl.* 1984, 23, 796; Takahasi et al., Tetrahedron Lett. 1989, 30, 1583; Ohta, H., Tetsukawa, H. *J. Chem. Soc. Chem. Commun.* 1978, 849). Enzymatic epoxidation methods remain impractical in comparison with synthetic organic chemistry approaches.

a. Cytochrome P-450

The cytochrome P-450 monooxygenase family has been used for epoxidation catalysis both with purified enzymes isolated from mammalian, microbial and plant sources and with partially purified liver microsomal preparations. The stereochemical course and the enantioselectivity of the P-450 reactions have been examined in some instances.

Wislocki and Lu (1982 *Proc. Natl. Acad. Sci. USA* 79, 6802–6806) studied the epoxidation of 8-methylbenz-[a]anthracene and showed that cytochromes P-450 and P-448 catalyze epoxidation at different faces of the 8,9-double bond. In 1982, Gelb et al. (1982 *Biochem. Biophys. Res. Commun.* In 1983 Ortiz de Montellano et al. (1983 *J. Biol. Chem.* 258, 4208–4213) examined the stereochemistry of the epoxidation of 1-octene by cytochrome P-450. This reaction concurrently produced 1,2-oxidooctane and N-alkylation of the heme prosthetic group by the activated epoxide or the olefinic intermediate. Stereochemical analysis showed that the S (or −) enantiomer of the trans epoxide is formed in slight excess over the R (or +) enantiomer.

Yang and Chiu (1985 *Arch. Biochem. Biophys.* 240, 546–552) and Yang (1988 *Biochem. Pharmacol.* 37, 61–70) showed that cytochrome P-450 preparations have varying degrees of stereoselectivity in catalyzing epoxidation reactions at various double bond positions in a variety of polycyclic aromatic hydrocarbons.

Wistuba et al. (1989 Chirality 1, 127–136) detected partial enantioselectivity in the in vitro conversion of simple prochiral and chiral aliphatic alkenes into oxiranes by liver microsomes. The enantiomeric excess of the epoxides extended from 0% for trimethyloxirane to 50% for ethyloxirane.

The P-450 enzymes are not appropriate for large scale epoxide synthesis. They require a continuous supply of NADH plus an accessory enzyme in order to transfer reducing equivalents from NADH to the P-450 enzyme, and they are not highly enantioselective.

b. Other Enzymatic Epoxidations

Various oxidative enzymes and heine proteins have been tested for activity in catalyzing epoxidation reactions. Hemoglobin and myoglobin have limited activity in catalyzing epoxidations. Methemoglobin and metmyoglobin catalyze the hydrogen peroxide depended oxidation of styrene to styrene oxide and benzaldehyde. Equal amounts of the R and S enantiomers are formed (Capdevila et al., 1990 *J. Biol. Chem.* 265, 10865–10871).

Horseradish peroxidase (Ortiz de Montellano and Grab, 1987 *Biochemistry* 26, 5310–5314) is capable of catalyzing the cooxidation of styrene when supplemented with hydrogen peroxide and an oxidizable phenol. The key features of the reaction involve first the oxidation of the phenol to a free radical which in turn reacts with molecular oxygen to generate the peroxy radical. The peroxy radical then reacts with styrene to form the epoxide.

The stereoselectivity of the epoxidation of 7,8-dihydroxy-7,8-dihydrobenzo[a]pyrene by prostaglandin H synthase has been examined. The synthase showed little selectivity (Panthananickal et al., 1983 *J. Biol. Chem.* 258, 4411–4418).

Myeloperoxidase is capable of catalyzing epoxidation reactions. It generates primarily anti-diolepoxides from trans-7,8-dihydroxy-7,8-dihydrobenzo[a]pyrene in the presence of hydrogen peroxide. The anti/syn ratio of the anti-diolepoxides is greater than 5, suggesting that the epoxidation proceeds via peroxyl radical or a ferryl oxygen transfer-mediated reaction (Mallet et al., 1991 *Carcinogenesis* 12, 521–524).

The availability of these enzymes is limited. Moreover, most catalyze cooxidation reactions in which a cosubstrate is oxidized to form a peroxy radical intermediate which then chemically reacts with the olefin to form the epoxide product. Most enantioselectivity is lost in the cooxidation reactions. In short, these reactions are not highly enantioselective.

c. Cell cultures

The conversion of alkenes to epoxides by whole cell cultures of microorganisms has been reported. Ohta and Tetsukawa (1978 *J. C. S. Chem. Comm.*, pp 849–850) studied the epoxidation of long-chain terminal olefins by whole cell cultures of *Corynebacterium equi.* They demonstrated the conversion of hexadec-1-ene (n-$C_{14}H_{29}CH=CH_2$) to its corresponding R-(+) epoxide. Also, May and Schwartz (1974 *J. Amer. Chem. Soc.* 96:4031–4032) have shown that cell cultures of *Pseudomonas oleovorans* convert 1,7-octadiene to (R)-(+)-7,8-epoxy-1-octene. The *P. Oleovorans* cells contain a P-450 monooxygenase.

Stirling and Dalton (1979 FEMS Microbiology Letters 5:315–318) have shown that whole cell cultures of *Methylococcus capsulatus* (Bath) are capable of converting ethylene, propylene, 1-butene, and cis- and trans-2-butene to epoxides when supplied with formaldehyde as a cosubstrate.

Hou et al. (1979 App. and Envir. Microbiol. 38:127–134) isolated a number of methane-utilizing microbes and showed that resting cell-suspensions of 3 organisms (*Methylosinus trichosporium, Methylococcus capsulatus* and *Methylobacterium organophilum*) were capable of oxidizing $C_2$ to $C_4$ n-alkenes to their corresponding 1,2-epoxides.

De Smet et al. (1981 App. and Envir. Microbiol, 42:811–816) have shown that under optimum conditions, resting and growing cultures of *Pseudomonas oleovarans* convert 1-octene to 1,2-epoxyoctane.

Furuhashi et al. (1981 E. J. Appl. Microbiol. Biotechnol. 12:39–45) have shown that a gaseous hydrocarbon-assimilating microorganism, *Nocardia corallina*, grew on 1-alkenes ($C_3$, $C_4$ and $C_{13}$ to $C_{18}$) and produced corresponding 1,2-epoxyalkanes.

Fu et al. (1991 *J. Am. Chem. Soc.* 113,5878–80) reported that *P. oleovarans* cultures were unable to oxidize internal olefins and disubstituted terminal olefins.

d. Chloroperoxidase

Chloroperoxidase (CPO) is known to catalyze some olefin epoxidation reactions under certain conditions. Morris, D. R.; Hager, L. P. *J. Biol. Chem.* 1966, 241, 3582; Blanke, S. R.; Yi, S.; Hager, L. P. *Biotechnology Lett.* 1989, 11, 769. CPO catalyzes the classical one electron oxidations typical of plant peroxidases and possesses a potent catalase activity (Thomas, J. A.; Morris, D. R.; Hager, L. P. *J. Biol. Chem.* 1970, 245, 3129 and Ortiz de Montellano, P. R.; Choe, Y. S.; De-Phillis, G.; Catalano, C. E. *J. Biol. Chem.* 1987, 262, 11641). CPO is similar to the P-450 cytochromes in that it catalyzes epoxidation and N-demethylation reactions (Kedderis, G. L.; Hallenberg, P. F. *Arch. Bioch. Biophys.* 1984, 233, 315). However, CPO utilizes $H_2O_2$ whereas the P-450 enzymes utilize molecular oxygen and require a regenerable reducing reagent, usually NADH.

McCarthy and White (1983 *J. Biol. Chem.* 258, 9153–9158) used chloroperoxidase in the enzymatic oxidation of cyclohexene to its epoxide in the presence of hydrogen peroxide. Subsequently, Geigert et al. (1986 24 Biochem. Biophys. Res. Commun. 136, 778–782) used chloroperoxidase to catalyze epoxidation of propylene, allyl chloride, 1,3-butadiene, cyclopentene and styrene. These investigators found that under their reaction conditions, the enzyme was generally rapidly inactivated.

Ortiz de Montellano et al. (1987 J. Biol Chem. 262, 11641–11646) used chloroperoxidase and hydrogen peroxide to oxidize styrene to styrene oxide and phenylacetaldehyde. Using trans-[1-$^2$H]styrene they showed that the tram epoxide isomer was the product of the oxidation.

Elfarra et al. (1991 *Arch. Bioch. Biophy.* 286, 244–251) has demonstrated the NADPH-dependent oxidation of 1,3-butadiene by mouse liver microsomes and the hydrogen peroxide-dependent oxidation of 1,3 butadiene by chloroperoxidase. Both oxidations yielded butadiene monoxide and crotonaldehyde.

Asymmetric oxidation of sulfides catalyzed by CPO has been discovered recently. (Collonna et al., *Tetrahedron: Asymmetry.* 1992, 3, 95). However, CPO catalyzes a variety of peroxidative halogenation reactions that are not enantioselective. (Hager et al., *J. Biol. Chem.* 1966, 241, 1769). CPO-catalyzed halogenation of alkenes has been shown to result in a racemic mixture of enantiomers.

For example, when chloroperoxidase is supplied with chloride ion, hydrogen peroxide and cis or trans pro-phenylphosphonic acid, there is no stereoselective synthesis of the corresponding halohydrins (Kollonitsch et al., 1970 J. Am. Chem. Soc. 92, 444489–90). Likewise, chloroperoxidase produces racemic bromohydrins when propylene and styrene serve as halogen acceptors (Neidleman, S. L., and J. Geigert 1986 Biohalogenation: Principles, Basic Roles and Applications. John Wiley and Sons, publisher, page 109).

Also, Ramakrishnan et al. (1983 Biochemistry 22, 3271–3277) showed nearly complete lack of stereoselectivity in the reaction of 2,methyl-4-propylcyclopentane-1,3-dione to the corresponding chlorinated compound. CPO is neither regiospecific or stereospecific in these cases.

In short, despite substantial research efforts worldwide, no reliable method of enantioselective chloroperoxidase-catalysed epoxidation of alkenes has previously been developed. Such a method, and the enantiomerically pure epoxides it produces, is very desirable for many purposes, including chemical synthesis of chiral products.

SUMMARY OF THE INVENTION

According to the invention, under certain conditions, chloroperoxidase is effective for the enantioselective catalytic epoxidation of a variety of olefins. The method of the invention is highly enantioselective, is able to produce substantially pure enantiomer product, has a high turnover rate, .and maintains the stability of a chloroperoxidase catalyst. The method of the invention is able to produce water soluble epoxides, works with a wide variety of olefins without destroying the catalyst, and allows high substrate to catalyst ratios. The newly accessible enantiomerically enriched epoxides according to the invention may be elaborated synthetically to provide new enantiomeric products in a wide range of applications.

According to the invention, an alkene substrate is combined with a non-alkaline solution of chloroperoxidase. A substrate oxidant, preferably hydrogen peroxide, is added gradually and the reaction is allowed to proceed until completion. The method of the invention may employ a cosolvent that promotes the interaction of the enzyme and the substrate, such as acetone or a detergent.

The olefin substrate may be an aliphatic alkene or an aryl alkene. Accordingly, it may be a straight chain, branched chain, monocyclic, or polycyclic aliphatic alkene, and it may be an alkene with phenyl or other aromatic constituents. The substrate may be a cyclic alkene fused with aromatic constituents, and it may have more than one alkene double bond, depending on steric considerations and the substrate's ability to produce a chiral epoxide product. Preferably, the substrate is a straight or branched aliphatic alkene having no more than 10 carbon atoms. When cyclic aliphatic or aryl alkenes are used as substrates, they may have as many as 30 carbons, but preferably less than 15 carbons. It is preferred that the constituents bound to the allylic carbons (those forming the double bond) are in the cis, rather than trans, isomeric configuration. Secondary, tertiary, or higher order alkenes (those with an internal double bond) are preferred to primary alkenes (with a terminal double bond).

The product of the invention is an enantiomerically enriched straight or branched chain epoxide preparation produced from olefin substrates by the method of the invention. The epoxides of the invention are preferably derived from unsubstituted alkenes, that is those with only a hydrocarbon component. The preparation is a substantially or essentially pure enantiomeric preparation of an asymmetrical epoxide having preferably no more than 10 carbons, with the epoxy group in a non-primary position.

BRIEF DESCRIPTION OF THE DRAWINGS

FIG. 1 is a proposed model for the interaction of an alkene substrate with the active site of chloroperoxidase to produce a chiral epoxide.

DETAILED DESCRIPTION

When an alkene, cis-$\beta$-methylstyrene, was incubated with chloroperoxidase (CPO) at room temperature in the presence of a low concentration of $H_2O_2$ in citrate buffer (ph=5), the reaction resulted in the stereoselective formation of one of the two possible enantiomeric cis-epoxides. If excess hydrogen peroxide was initially present in the buffered enzyme solution when substrate was added, alkene conversion proceeded only to <5% before the enzyme was completely inactivated, but enantioselectivity in epoxide formation was high (92% ee).

CPO has a tendency to undergo irreversible decomposition in the presence of $H_2O_2$. Accordingly, conditions were sought under which such decomposition would not occur, so as to increase the number of turnovers of the CPO molecules. It was determined that a stable reaction mixture could be produced if the concentration of the substrate oxidant is maintained at a minimum during the course of epoxidation. Indeed, when $H_2O_2$ was provided to the system via syringe pump in a continuous and slow addition (2–10$\mu$l/min), up to 70% substrate conversion was attained using 0.046 mol % (the molar ratio of enzyme to substrate) of the enzyme, and enantioselectivity remained high. Complete substrate conversion could be achieved with the use of higher initial enzyme concentration (0.138 mol %), and the enantioselectivity in epoxidation was also measurably improved under these conditions (up to 97% ee).

Although the protocol described above proved satisfactory for epoxidation of cis-$\beta$-methylstyrene, this olefin proved to be uniquely reactive under these conditions and other alkenes benefitted from use of a cosolvent to improve the reactivity as well as the selectivity of the enzyme. The cosolvent may increase substrate solubility, as with acetone, or form micelles, as with certain detergents, so as to increase the interaction between substrate and enzyme. A preferred cosolvent is acetone. A preferred concentration is around 25%.

For example, cis-2-heptene was oxidized to the corresponding epoxide with 60% conversion and 90% ee in citrate buffer, while under the same conditions substrate conversion was complete and epoxide was generated in 96% ee in acetone/citrate buffer medium.

Accordingly, another embodiment of the invention is as follows. Chloroperoxidase was obtained and its concentration assayed by the published procedure (Morris, D. R.; Hager, L. P. *J. Biol. Chem.* 1966, 241, 3582). All other reagents and solvents were used as received from commercial suppliers. Acetone (15 mL) was added to citrate buffer (0.1 M, 45 mL, pH 5), resulting in a clear solution.

An alkene, cis-2-heptene (Wiley, 49 rag, 0.5 retool), was added to this solution. The mixture was stirred vigorously at room temperature for 1–2 rain, after which the CPO solution (2mL, 4.8 mg/mL, 0.046 mol %) was added. Stirring was sustained as undiluted 30% $H_2O_2$ was added at a rate of 2 $\mu$l/min via a syringe pump and the progress of the reaction was followed by gas chromatography (GC). After 2h of continuous addition, disappearance of olefin was complete and the epoxide was present as the only detectable product.

The aqueous solution was extracted with ether/pentane (1:1 v/v, 2×50 mL) and the combined organic phases were dried over $Na_2SO_4$. The epoxide was not isolated due to its volatility, but the yield was determined to be 82% by GC analysis using dodecane as a quantitative internal standard. The enantiomeric excess of the epoxide was determined to be 96% by capillary gas chromatography. Yield and enantiomeric excess may be measured by the method of Ortiz de Montellano et al., (1987 *J. Biol. Chem.* 262:11641) or other known methods. Peak ratios were established by electronic integration.

Enantiomeric excess is a measure of the difference between the percentage of the two enantiomers. Thus, an enantiomeric excess of 0% represents a racemic mixture, 50% represents a mixture in which 75% of the epoxide molecules are one enantiomer, 90% represents a 95/5 mixture, and 100% represents a pure enantiomeric preparation.

The enantiomeric purity achieved by the invention varies. Some preparations with low enantiomeric excess may be called partially enantiomerically pure. Those with ee over about 80% are substantially enantiomerically pure, and a preparation with ee over about 90% is essentially enantiomerically pure. All may be called "enantiomerically pure" according to the invention. Enantiomeric purity is not relate to overall purity, and enantiomerically pure preparations may have other components such as solvents, cosolvents, mixants, carriers, stabilizers, and so on.

The preferred concentration of the substrate may range from about 0.05 mmol to about 5 mmol. The most preferred range is from about 0.1 mmol to about 1 mmol.

The preferred concentration of CPO may range from about 0.01 $\mu$mol to about 10 $\mu$mol. A most preferred range is from about 0.1 $\mu$mol to about 0.5 $\mu$mol. A preferred range expressed in terms of mole percent (the molar ratio of CPO to substrate) is about 0.4 mol % to about 1.2 mol %. The ratio of alkene substrate to CPO concentration may range up to about 10,000:1 or higher, and is preferably about 1,000:1. The higher substrate/CPO ratios are obtainable with a stable reaction mixture, high turnover rates and number of turnovers per enzyme molecule, and appropriate substrates.

The substrate oxidant serves as the stoichiometric source of oxygen in the conversion of the olefinic carbon-carbon double bond to the epoxide moiety. Hydrogen peroxide is the preferred substrate oxidant. Other effective substrate oxidants might be employed instead of hydrogen peroxide. Other peroxide-based oxidants that may be used include methyl and ethyl peroxide, meta-chloroperoxybenzoic acid, and peracetic acid or other small organic peroxy compounds. Some substrate oxidants (like t-butyl hydrogen peroxide and iodosylbenzene) are too bulky or otherwise ineffective for CPO-catalyzed epoxidations.

The preferred concentration for substrate oxidant is one that optimizes the speed of reaction and the stability of the CPO enzyme. The oxidant is preferably added gradually in a continuous stream so that it is consumed at approximately the same rate as it is added. Accordingly, the oxidant concentration is maintained at a low level that avoids a substantial excess of the substrate oxidant.

Various buffers may be used, and the pH is preferably kept non-alkaline. At about pH 7, CPO denatures and loses its activity. A most preferred buffer is citrate, because it contributes to the stability of the CPO. The concentration of buffer may range between about 0.001 M and 1M, and a preferred concentration is about 0.1 M.

The enantiomeric purity achieved by the invention varies. Some preparations with low enantiomeric excess may be called partially pure. Those with ee over about 80% are substantially pure, and a preparation with ee over about 90% is essentially pure. All may be called "pure" according to the invention.

Olefin substrates may be primary, secondary, or higher order alkenes. Primary olefins are less preferable than the internal alkenes. The olefins may be straight chain, branched chain, monocyclic or polycyclic compounds, and may include alkyl, aryl, or arylalkyl groups. Under some conditions, the olefins may be substituted with functional groups. In order to achieve chiral synthesis, the olefins must be asymmetric, meaning that the constituents on one side of the double bond are different from those on the other.

Cyclic olefins (alkyl or arylalkyl) having up to 30 carbons, but preferably no more than 15, may be employed as substrates. With straight and branched olefins, compounds having nine or more carbon atoms can be used, but they are relatively poor substrates, presumably due to size restrictions in the active site.

For example, under the conditions of example 12, below, the following substrates were largely non-reacting: cis-3-nonene, cis-4-decene, cis-3-decene, 2-methyl-2-octene, and cis-2-decene. Some trisubstituted olefins were also non-reactive under the conditions in example 12, such as 2,2-dimethyl-3-hexene and 4,4-dimethyl-2-pentene. Some substrates tended to inactivate the CPO more rapidly than their conversion to epoxides. These include allyl chloride, allyl benzene, 1-hexene, and 1-pentene.

Other substrates that did not provide practical yields under the same conditions were allyl alcohol; and the substituted alkenes, allyl amine and cis-ethyl cinnamate. Presumably, the hydrophobic nature of the substrates is important to the ability of the enzyme to carry out the epoxidation reaction, and indeed polar hydrophilic constituents such as oxygen, nitrogen, sulfur, and halogens tend to interfere with the effective production of chiral epoxides.

Other conditions consistent with the invention would enable enantioselective conversion of such difficult substrates. Like terminal (primary) alkenes which were also found to be generally poor substrates, trans- olefins are converted to enantiomeric epoxides by the method of the invention, but were found to be relatively poor substrates with regard to both reactivity and enantioselectivity.

Steric considerations in epoxidation reactions mediated by heine proteins provide a possible explanation for the relatively poor conversion of the foregoing substrates. Referring to FIG. 1, it is proposed that the heine prosthetic group at the active site of the CPO molecule includes an oxyferryl pi cation radical of iron protoporphyrin IX and is generally planar. Alkenes in the cis-configuration are able to approach a planar surface, and hence fit in better, than alkenes in the trans- configuration. Likewise, aliphatic alkenes over nine carbons long, trisubstituted alkenes, and aryl alkenes with over 15 carbons may have steric factors restricting their access to the active site as compared with secondary alkenes and smaller and less substituted alkenes.

According to the model depicted in FIG. 1, and not by way of limitation of the invention, the asymmetric alkene substrate has a large side and a small side. The configuration of the active site is thought to orient the alkene on the basis of its asymmetry so that the oxygen molecule is added predominantly to only one side—below the alkene, as depicted. As a result, substantially only one enantiomer is formed. If the alkene were able to freely approach the active site in the reverse orientation as well, the two enantiomers would be formed in equal proportions, and the preparation would be racemic.

Adjustment of the reaction conditions according to the invention and known methods can enhance the yield for particular alkenes. In some cases, it may be necessary to modify the CPO active site, for example by site specific mutagenesis of the gene for the CPO enzyme in the fungus Caldariomyces fumago, or according to other known methods. A modified CPO may be able to increase substrate conversion, yield, and enantiomeric excess for epoxides formed from the more difficult substrates.

Indeed, the method of the invention may also permit enantioselective epoxidation of functionalized and substituted alkenes as well as nonfunctionalized alkenes. Moreover, consistent with the invention, the CPO active site can be modified by genetic engineering of the cloned CPO gene. This approach might be employed to reverse chirality, so that a pure preparation of either enantiomer of the epoxide may be obtained as desired for purposes of preparing a final sterioisomer product or an optically active intermediate.

The products of the invention are enantiomerically enriched epoxide preparations produced by the method of the invention. The epoxides of the invention are derived from unsubstituted alkenes, that is those with only a hydrocarbon component. The chiral epoxide preparations of the invention comprise substantially or essentially enantiomerically pure preparations of asymmetrical epoxides, having between 4 and 30 carbons. Preferably, the epoxide has between 4 and 15 carbons, with the epoxy group in a non-primary position, wherein the constituents attached to the epoxy group are selected from the group consisting of hydrogen, unsubstituted straight chain and branched C1 to C7 alkyl groups, cyclic alkenes, and aryl groups. Most preferably, with epoxides having only non-cyclic aliphatic constituents, the epoxide has no more than 9 carbons.

In structural terms, the products of the invention are preparations of enantiomerically enriched epoxide having the formula

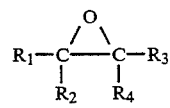

wherein the R constituents are selected from the group consisting of hydrogen, alkyl groups, and aryl groups; at least one of the R groups on each side of the epoxy group is different from the R groups on the other side so that the epoxide is asymmetric; at least one of $R_1$ and $R_2$ and one of $R_3$ and $R_4$ is an alkyl or aryl group; and the total number of carbons in the epoxide is less than 30. Where the Preferably, one R group on each side of the epoxy group is hydrogen, and the other two R groups are in the cis-configuration.

In some epoxide preparations, the R groups on one side of the epoxy group may be part of the same cyclic constituent, or the R groups on opposite sides of the epoxy group may be part of the same cyclic constituent.

The epoxide may be converted to a chiral diol in accordance with the invention, or to other chiral products by methods known in the art. Compared with previously reported enzymatic and microbial epoxidation methods, the CPO-based system appears to accept a broader range of substrates and to effect epoxidation with generally much higher enantioselectivities. One important advantage of this approach is that it is highly complementary to existing asymmetric epoxidation protocols involving either synthetic or biological catalysts, which are ineffective with most of the substrates in Table I.

TABLE I

Asymmetric Epoxidation Reactions Catalyzed by CPO.[a]

| Entry | Substrate | ee (%) | Epoxide Config | Substrate Conv (%) | Epoxide Yield (%) |
|---|---|---|---|---|---|
| 1 |  CH$_3$ — n-C$_4$H$_9$ | 96 | 2R,3S[b] | 100 | 78 |
| 2 |  CH$_3$ — n-C$_5$H$_{11}$ | 92 | 2R,3S[c] | 96 | 82 |
| 3 |  CH$_3$ — n-C$_3$H$_7$ | 97 | 2R,3S[c] | 17 | 12 |
| 4 |  CH$_3$ — n-C$_6$H$_{13}$ | — | — | — | — |
| 5 |  n-C$_6$H$_{11}$ | — | — | — | — |
| 6 |  CH$_3$ — i-C$_4$H$_9$ | 94 | 2R,3S[e] | 53 | 33 |
| 7[d] |  CH$_3$ — i-C$_3$H$_7$ | 66 | 2R,3S[e] | 100 | 28 |
| 8 |  CH$_3$ / n-C$_6$H$_{11}$ | 74 | n.d. | 10 | n.d. |
| 9 |  CH$_3$ — C$_2$H$_5$ / CH$_3$ | 81 | n.d. | −50[e] | n.d. |
| 10[d] |  Ph — CH$_3$ | 96 | 1S,2R[f] | 73 | 67[g] |
| 11[h] | 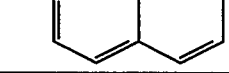 | 97[i] | 1R,2R[i] | 100 | 85[f] |

[a]Reactions were run, and ee's and yields were determined as described unless otherwise noted, using 0.03–0.12 mol % of the enzyme.
[b]Epoxide configuration assigned by correlation to R-(−)-2-heptanol.
[c]Epoxide absolute configuration tenatively assigned by analogy to entry 1.
[d]Reaction run in the absence of acetone as cosolvent.
[e]Accurate measurement not achieved due to overlapping GC signals from solvent.
[f]Epoxide configuration assigned by correlation to pseudoephedrine: Witkop, B.; Foltx, C. M. J. Am. Chem. Soc. 1957, 79, 197.
[g]Isolated yield.
[h]Trans-diol isolated as secondary product due to uncatalyzed epoxide hydrolysis.
[i]Of trans diol. Absolute configuration assigned by correlation to (1R,2S)-(+)-dihydronaphthalene oxide.

EXAMPLE 1

This example shows the stereospecific conversion of cis-olefins to the corresponding cis-epoxides observed with very high enantioselectivity. A reaction was run according to the general method described above using cis-2,3-heptene and acetone. The ratio of CPO to substrate in this and the next examples was 0.03 tool% to 0.12 mol %. (Table 1, entry 1.) The enantiomeric excess was analyzed as described above, and was 96%, an essentially pure enantiomeric preparation. The epoxide configuration was determined to be 2R,3S by correlation to R-(−)-2-heptanol. The substrate conversion was 100%, indicating that no substrate was left in the reaction mixture. The net epoxide yield was 78%.

EXAMPLE 2

Under similar conditions as in Example 1, cis-2,3-n-octene was used as a substrate. (Table 1, entry 2.) The enantiomeric excess was 92%, an essentially pure enantiomeric preparation. The epoxide configuration was assumed by analogy to be the same as in example 1. The substrate conversion was 96%, and the epoxide yield was 82%.

EXAMPLE 3

This example shows the highly efficient and stereospecific epoxidation of a secondary cis-alkene with a long chain. Under similar conditions as in Example 1, cis-3,4-n-heptene was used as a substrate. (Table 1, entry 3.) The enantiomeric excess was 97%, representing an essentially pure enantiomeric preparation. The epoxide configuration was assumed by analogy to be the same as in example 1. The substrate conversion was 17%, and the epoxide yield was 12%.

It is possible that steric considerations restrict the interaction of the heptene with the active site of the CPO, thus reducing the yield. Adjustment of reaction conditions, including rate of addition of peroxide, use of cosolvents, and modification of the CPO active site can increase the conversion and yield.

EXAMPLE 4

This example shows that when the total linear carbons reach nine, the epoxide yield from the reaction is reduced as compared to substrates with shorter chains. Under similar conditions as in Example 1, cis-2,3-n-nonene is used as a substrate. (Table 1, entry 4.) There is a substantial enantiomeric excess. The substrate conversion and epoxide yield are relatively low.

EXAMPLE 5

This example shows that primary alkenes are less productive substrates than secondary alkenes. The same procedure is carried out using 1,2-n-octene. (Table 1, entry 5.) The enantiomeric excess is substantial, but less than in example 2, as are the yields and conversion percent.

EXAMPLE 6

This example shows that branched alkenes make satisfactory substrates for conversion to their corresponding epoxides. (Table 1, entry 6.) Cis-2,3-i-heptene was used as a substrate under similar conditions as described in the preceding examples. An essentially pure enantiomeric epoxide preparation was produced, with enantiomeric excess of 94%. Substrate conversion was 53% and epoxide yield was 33%.

EXAMPLE 7

This example also shows that substrates having branching on the alkyl substituents make satisfactory substrates for conversion to their corresponding epoxides, although substrate conversion and enantioselectivity were affected by the position of branch (Table 1, entry 7.) Cis-2,3-i-hexene was used as a substrate under similar conditions as described in the preceding examples, except acetone was used as a cosolvent. A substantially pure enantiomeric epoxide preparation was produced, with enantiomeric excess of 66%. Substrate conversion was 100%, but yield was only 28%.

EXAMPLE 8

This example also shows that disubstituted primary alkenes are effective substrates for conversion to their corresponding epoxides. (Table 1, entry 8.) 2-methyl-1,2-n-octene was used as a substrate under similar conditions as described in the preceding examples, without a cosolvent. A substantially pure enantiomeric epoxide preparation was produced, with enantiomeric excess of 74%. Substrate conversion was only 10% and yield was not determined. As compared with example 2, the primary alkene is less efficiently oxidized than the secondary alkene.

EXAMPLE 9

Certain trisubstituted olefins, meaning those with three constituents around the carbon-carbon alkene double bond, were also good substrates for catalytic epoxidation CPO with moderate-to-good enantioselectivity in epoxidation. This is shown for 3-methyl-2,3-cis-pentene. (Table 1, entry 9.) Epoxidations proceeded to low conversion before enzyme inactivation. However, substantially pure enantiomeric epoxide was produced.

EXAMPLE 10

This example shows effective stereospecific epoxidation of alkenes with aromatic constituents. (Table 1, entry 10.) Cis-$\beta$-methylstyrene was converted to an essentially pure enantiomeric epoxide preparation using the preceding method with acetone cosolvent. Substrate conversion and epoxide yield were high.

EXAMPLE 11

This example shows effective stereospecific epoxidation of another aromatic substrate, in this case the fused double ring aryl alkene dihydronaphthalene, a cis-disubstituted cyclic alkene with aromatic constituents. (Table 1, entry 11.) Dihydronaphthalene was oxidized cleanly and the epoxide reacted to afford the corresponding fused double ring trans- diol. It is believed that the reaction involves an uncatalyzed and highly selective hydrolytic ring opening of the acid-sensitive epoxide. The alkene was converted to an essentially pure enantiomeric trans diol preparation. Substrate conversion and diol yield were high.

EXAMPLE 12

In this example, 0.5 mmol of the substrate, cis-2,3-n-hexene, was reacted with $1.6\times 10^{-4}$ mmol CPO, and hydrogen peroxide was pumped in at a rate of 0.008 to 0.08 mls/min. The reaction was run at pH 5.0 in 30 mls of 25% acetone/0.1M citrate. Reaction time was 2 to 4 hours. An essentially pure preparation of epoxide was produced, in enantiomeric excess of greater than 97%. In this example and those that follow, in some cases in order to receive the highest possible yield, the enzyme concentration was increased up to $4.8\times 10^{-4}$ mmol.

EXAMPLE 13

In this example, trans-2,3-n-octene was reacted as in example 12, but without acetone. Conversion was only about 6%. A higher degree of conversion must be achieved in order to provide a practical method of producing pure enantiomeric epoxides.

EXAMPLE 14

In this example, styrene was reacted as in example 13. Conversion was not determined, but enantiomeric excess was about 50%, representing a substantially pure enantiomeric preparation. It should be noted that in this example, as in many others, the substrate is not chiral; that is, it does not exist in enantiomeric form. The substrate is asymmetric, however, and the resulting epoxides are enantiomeric because they have four different constituents bound to at least one of the epoxyl carbons (corresponding to the allyl double-bound carbon of the alkene).

EXAMPLE 15

In this example, 1-methyl-1,2-cyclohexene was reacted as in example 13. Conversion was only about 5%. Enantiomeric excess was about 21%, representing a partially pure enantiomeric preparation.

The foregoing description of the preferred embodiments of the invention has been presented for purposes of illustration and description. It is not intended to be exhaustive or to limit the invention to the precise forms disclosed. Many modifications and variations are possible in light of the above teaching. All such embodiments which do not depart from the spirit and scope of the invention are intended to be covered, consistent with the claims which follow.

We claim:

1. A method of converting olefins to chiral epoxides, comprising (a) combining an asymmetric alkene substrate with a non-alkaline chloroperoxidase solution, and (b) adding an effective substrate oxidant to form a stabilized reaction mixture, such that the oxidant is maintained at a concentration that does not produce a substantial oxidant excess, and the chloroperoxidase catalyzes the conversion of the substrate to the corresponding epoxide in enantiomeric excess.

2. The method of claim 1 wherein the pH of the reaction mixture is no greater than about 5.

3. The method of claim 1 wherein the reaction mixture further comprises a citrate buffer.

4. The method of claim 1 wherein the substrate oxidant is a peroxide selected from the group comprising hydrogen peroxide, methyl peroxide, ethyl peroxide, meta-chloroperoxybenzoic acid, or peracetic acid.

5. The method of claim 1 wherein the substrate oxidant is hydrogen peroxide.

6. The method of claim 1 wherein the substrate oxidant is added gradually.

7. The method of claim 1 wherein the reaction mixture further comprises a cosolvent.

8. The method of claim 1, further comprising the step of adding a cosolvent that promotes the interaction of the enzyme and the substrate.

9. The method of claim 1 wherein the alkene double bond is in an internal position.

10. The method of claim 1 wherein the alkene is in the cis-configuration.

11. The method of claim 1 wherein the alkene substrate is selected from the group consisting of straight chain and branched chain aliphatic alkenes having up to about ten carbons, and mono-cyclic, polycyclic, and fused ring aliphatic and aryl alkenes having up to about 30 carbons.

12. The method of claim 1 wherein the alkene substrate is selected from the group consisting of straight chain and branched chain aliphatic alkenes having up to about nine carbons, and mono-cyclic, polycyclic, and fused ring aliphatic and aryl alkenes having up to about 15 carbons.

13. The method of claim 1 wherein the alkene is an aryl alkene compound having up to 15 carbons.

14. The method of claim 1 wherein the alkene is a cis-alkyl substituted styrene.

15. The method of claim 1 wherein the alkene is cis-$\beta$-methyl styrene.

16. The method of claim 1 wherein the alkene is a straight or branched chain alkyl compound and contains up to 9 carbon atoms.

17. The method of claim 1 wherein the alkene is a straight or branched chain alkyl compound at least four carbons long, and the double bond is in an internal non-primary position.

18. The method of claim 1 wherein the alkene is a primary olefin.

19. The method of claim 1 wherein the alkene is a primary olefin and contains a suitable electron withdrawing substituent capable of preventing the rapid inactivation of the chloroperoxidase.

20. The method of claim 1 wherein the alkene is sufficiently sterically planar to allow stereoselective conversion to epoxide by chloroperoxidase.

21. The method of claim 1 wherein the CPO is modified to enhance conversion of alkenes to enantiomeric epoxides.

22. The method of claim 8, wherein the cosolvent is acetone.

* * * * *